United States Patent
Ueki

(10) Patent No.: US 8,676,740 B2
(45) Date of Patent: Mar. 18, 2014

(54) ATTRIBUTE ESTIMATION SYSTEM, AGE ESTIMATION SYSTEM, GENDER ESTIMATION SYSTEM, AGE AND GENDER ESTIMATION SYSTEM AND ATTRIBUTE ESTIMATION METHOD

(75) Inventor: Kazuya Ueki, Koto-ku (JP)

(73) Assignee: NEC Soft, Ltd., Tokyo (JP)

( * ) Notice: Subject to any disclaimer, the term of this patent is extended or adjusted under 35 U.S.C. 154(b) by 1024 days.

(21) Appl. No.: 12/680,735

(22) PCT Filed: Sep. 18, 2008

(86) PCT No.: PCT/JP2008/066878
§ 371 (c)(1),
(2), (4) Date: Mar. 29, 2010

(87) PCT Pub. No.: WO2009/041349
PCT Pub. Date: Apr. 2, 2009

(65) Prior Publication Data
US 2010/0217743 A1      Aug. 26, 2010

(30) Foreign Application Priority Data
Sep. 28, 2007   (JP) ................................. 2007-254295

(51) Int. Cl.
G06N 5/00  (2006.01)
G06F 1/00  (2006.01)

(52) U.S. Cl.
USPC .............................. 706/52; 600/473; 382/124

(58) Field of Classification Search
USPC .......................................................... 706/52
See application file for complete search history.

(56) References Cited

U.S. PATENT DOCUMENTS

| | | | |
|---|---|---|---|
| 2007/0081705 A1* | 4/2007 | Carneiro et al. | 382/128 |
| 2008/0235019 A1* | 9/2008 | Witzman | 704/251 |
| 2010/0056898 A1* | 3/2010 | McKenna et al. | 600/411 |

FOREIGN PATENT DOCUMENTS

| | | |
|---|---|---|
| JP | 3-232064 A | 10/1991 |
| JP | 11-175724 A | 7/1999 |
| JP | 2000-47673 A | 2/2000 |
| JP | 2002-330943 A | 11/2002 |
| JP | 2005-148880 A | 6/2005 |
| JP | 2005-250712 A | 9/2005 |
| JP | 2006-318375 A | 11/2006 |
| JP | 2007-48172 A | 2/2007 |
| JP | 2007-58828 A | 3/2007 |
| JP | 2007-203951 A | 8/2007 |

OTHER PUBLICATIONS

T. Hayashida, et al., "Consideration of a method for integrating multiple classifiers in estimating gender and age by a face image," The Institute fo Electonics, Information and Communication Engineers, ICICE Technical Report, PRMU2005-96, Oct. 2005, pp. 19-24, vol. 105, No. 375.

* cited by examiner

*Primary Examiner* — Kakali Chaki
*Assistant Examiner* — Kalpana Bharadwaj
(74) *Attorney, Agent, or Firm* — Sughrue Mion, PLLC

(57) ABSTRACT

An attribute estimation system and a method in which there are no cases that the estimation accuracy declines in a specific numerical value area, and an age estimation system, a gender estimation system and an age and gender estimation system using this is provided.

It is a system to estimate an age of a person photographed in an input image, the system including: a classifier 3 that estimates the age of a person as a discrete quantity based on data of an input image; a classifier 4 that estimates the age of a person as a continuous quantity based on data of an input image; and an integration unit 7 that integrates an estimated result of the classifier 3 and an estimated result of the classifier 4.

20 Claims, 18 Drawing Sheets

SCORE OF DISCRETE QUANTITY

SCORE OF CONTINUOUS QUANTITY

SCORE OF THE 20s BASED ON CRITERION DATA

SCORE OF 23.5 YEARS OLD BASED ON CRITERION DATA

SCORE AFTER INTEGRATION

ATTRIBUTE ESTIMATION SYSTEM, AGE ESTIMATION SYSTEM, GENDER ESTIMATION SYSTEM, AGE AND GENDER ESTIMATION SYSTEM AND ATTRIBUTE ESTIMATION METHOD

TECHNICAL FIELD

The present invention relates to an attribute estimation system which estimates a value which is impossible to be measured physically, and in particular, relates to an attribute estimation system and an attribute estimation method in which there are no cases that the estimation accuracy declines in a specific numerical value area, and an age estimation system, a gender estimation system and an age and gender estimation system using this.

BACKGROUND ART

As a kind of system which estimates a value which is impossible to be measured physically based on a feature extracted from inputted information, there is a system that estimates the age and the gender of a person by extracting a feature of the person from inputted image data and comparing the extracted feature with data learned in advance.

For example, as shown in FIG. 1, a system having feature extraction units to extract a feature from an input image and a classifier which estimate an age by comparing the extracted feature with data learned in advance is related.

In the above-mentioned related system, as a classifier which processes an extracted feature to estimate an age, there is a case where an estimated result is handled as a discrete quantity like invention disclosed in patent document 1 and a case where it is handled as a continuous quantity like invention disclosed in patent document 2.

[Patent document 1] Japanese Patent Application Laid-Open No. 2007-58828
[Patent document 2] Japanese Patent Application Laid-Open No. 2005-148880

DESCRIPTION OF THE INVENTION

Problem to be Solved by the Invention

When an estimated result is handled as a discrete quantity, the estimated result is outputted as data indicating to which of classes divided into age groups it corresponds. For example, when age is divided into classes categorized as the 0s (0-9 years old), 10s (10-19 years old), 20s (20-29 years old), 30s (30-39 years old), 40s (40-49 years old), 50s (50-59 years old) and no smaller than 60 (60 years old or more), one of the class names such as "the 20s" or "the 50s" is selected and outputted as an estimated result.

However, in this case, there is a problem of how to classify age groups. For example, there is a problem about degree of width to divide the class, or about a reference (the median) to divide age groups (for example, even if 10-years-old width which is same as the above-mentioned example classification is employed, classification of such as 15-24 years old can be also considered).

Also, when 20s (20-29 years old) and 30s (30-39 years old) are separated, there is a problem that overall accuracy falls, because data of two ages such as 29 years old and 30 years old which have no large difference is forced to be separated.

When a specific feature cannot be extracted from an image, both the class into which the image is classified easily and the class into which the image is not classified easily occur. That is, although age can be estimated accurately about young age groups and old age groups in which specific features are easy to be observed, it is difficult to estimate accurately about rising generation groups and middle age groups in which specific features is not easy to be observed. Therefore, when a system that handles an estimated result as discrete quantity is applied to a customer base analysis in a store or the like, outputs for a specific class such as young age groups and old age groups increase, and outputs for a specific class such as rising generation groups and middle age groups reduce, and as a result the customer base cannot be analyzed accurately.

On the other hand, when an estimated result is handled as a continuous quantity, because a classifier learns such that a residual error may be minimized at the stage of learning, when an attempt to improve the overall performance is performed, a tendency for an estimated result to be drawn to the center appears. That is, there is a tendency in which the younger an age is than the average age, the older the age is estimated, and the older an age is than the average age, the younger the age is estimated, and thus it is difficult for ages of young age groups and old age groups to be estimated accurately.

Thus, there is a problem that precision of estimation of the age of a person in a specific age group becomes low in the above-mentioned related technology.

The present invention has been made in view of the above mentioned problem, and the object of the present invention is to provide an attribute estimation system and a method in which there are no cases that the estimation accuracy declines in a specific numerical value area, and an age estimation system, a gender estimation system and an age and gender estimation system using this.

Means for Solving the Problem

In order to achieve the above-mentioned object, the present invention provides, as a first aspect, an attribute estimation system which is a system to estimate an attribute about at least one piece of input data and which includes: a first estimation means which estimates the attribute as a discrete quantity based on the input data; a second estimation means which estimates the attribute as a continuous quantity based on the input data; and an integration means which integrates an estimated result of the first estimation means and an estimated result of the second estimation means.

Also in order to achieve the above-mentioned object, the present invention provides, as a second aspect, an age estimation system using an attribute estimation system according to the above-mentioned first aspect of the present invention, wherein at least one piece of input data is image data, and the attribute is an age of a person photographed in the image.

In order to achieve the above-mentioned object, the present invention provides, as a third aspect, a gender estimation system using an attribute estimation system according to the above-mentioned first aspect of the present invention, wherein at least one piece of input data is image data, and the attribute is a gender of a person photographed in the image.

In order to achieve the above-mentioned object, the present invention provides, as a fourth aspect, an age and gender estimation system using an attribute estimation system according to the above-mentioned first aspect of wherein at least one piece of input data is image data, and the attributes are an age and a gender of a person photographed in the image.

In order to achieve the above-mentioned object, the present invention provides, as a fifth aspect, an attribute estimation method for estimating an attribute about at least one piece of input data including: a first estimation step for estimating an attribute as a discrete quantity based on input data; a second estimation step for estimating an attribute as a continuous quantity based on input data; and an integration step for integrating an estimated result in the first estimation step and an estimated result in the second estimation step.

Advantageous Effect of the Invention

According to the present invention, an attribute estimation system and a method in which there are no cases that the estimation accuracy declines in a specific numerical value area, and an age estimation system, a gender estimation system and an age and gender estimation system using this can be provided.

BEST MODE FOR CARRYING OUT THE INVENTION

As shown in FIG. 2, an attribute estimation system according to the present invention is a system to estimate an attribute about at least one piece of input data and the system includes: a first estimation unit that estimates an attribute as a discrete quantity based on input data; a second estimation unit that estimates an attribute as a continuous quantity based on input data; and an integration unit which integrates an estimated result in the first estimation unit and an estimated result in the second estimation unit. Hereinafter, preferred embodiments will be described taking the case where an input data is image data and an attribute to be estimated is an age as an example.

The First Exemplary Embodiment

The first exemplary embodiment in which the present invention is implemented suitably will be described.

A structure of an age estimation system according to this exemplary embodiment is shown in FIG. 3.

This system has feature extraction units 1 and 2, classifiers 3 and 4, score-generation units 5 and 6 and an integration unit 7. It is possible to compose each of these units using exclusive hardware, and also they can be realized on a computer by a software processing.

The feature extraction unit 1 extracts a feature which is used by the classifier 3 for estimation of age from an input image. The feature extraction unit 2 extracts a feature which is used by the classifier 4 for estimation of age from the input image. The classifier 3 stores criterion data which has been already learned in advance and estimates the age of the person on an input image as a discrete quantity using the feature extracted from the input image by the feature extraction unit 1 and the criterion data. The classifier 4 stores criterion data which has been already learned in advance and estimates the age of the person on an input image as a continuous quantity using the feature extracted from the input image by the feature extraction unit 2 and the criterion data. The score-generation unit 5 generates a score of an estimated result (discrete quantity) outputted from the classifier 3. The score-generation unit 6 generates a score of an estimated result (continuous quantity) outputted from the classifier 4. The integration unit 7 integrates the scores outputted from each of the score-generation units 5 and 6. Meanwhile, a score is a value which indicates the correlation of a certain estimated result (discrete quantity and continuous quantity) outputted from a classifier and age information (the actual age and the appearance age of a target person of estimation). Details of processing of score generation will be described in the latter part of the following description.

Note that, the feature extraction unit 1, the classifier 3 and the score-generation unit 5 correspond to the first estimation unit 51 in FIG. 1. Also, the feature extraction unit 2, the classifier 4 and the score-generation unit 6 correspond to the second estimation unit 52 in FIG. 1. The integration unit 7 corresponds to an integration unit 53 in FIG. 1.

To the processing for estimating the age of a person from the feature using criterion data already learned by the classifiers 3 and 4, publicly known methods can be applied. To the classifier 3 that estimates the age of a person as a discrete quantity, techniques of such as the linear discriminant analysis (Liner Discriminant Analysis: LDA), the mixture Gaussian distribution model (Gaussian Mixture Model: GMM) and Support Vector Machine can be applied. To the classifier 4 that estimates the age of a person as a continuous quantity, techniques of such as the multiple regression analysis, the neural network and Support Vector Regression can be applied.

To the processing in which the feature extraction units 1 and 2 extracts a feature from an input image, publicly known methods can be applied and, more specifically, techniques such as the edge detection and the binarization can be applied.

The processing of the score-generation unit 5 which generates the score from the discrete quantity which is the estimated result outputted from the classifier 3 will be described. As mentioned above, the score is a value which indicates the correlation between a certain estimated result and age information, and the score is indicated as a linear function in a rectangular coordinate system in which age is adopted as the other axis. An example of generating the score when the classifier 3 selects any one of classes and outputs the estimated result is shown in FIG. 4. The vertical axis of graphs in this Figure represents score Sc of discrete quantity and the horizontal axis represents age. Here, a case when the discrete quantity of "the 20s" has been outputted from the classifier 3 as the estimated result is shown as an example.

In the case of (a), a score is generated such that it is a fixed value for ages of not less than 20 years old and less than 30 years old which correspond to the 20s. In the case of (b), a score is generated such that the highest value is assigned to 25 years old which is the median in the class of the 20s, and the larger the distance between the median and an age is, the more the score declines in a linear manner. In the case of (c), a score is generated such that it is of a shape of a normal distribution centering on 25 years old which is the median in the class of the 20s.

An example of generating the score when the classifier 3 outputs the estimated result as the probability corresponding to each class is shown in FIG. 5. Like FIG. 4, the vertical axis of graphs in this Figure represents score Sc of discrete quantity and the horizontal axis represents age. Here, a case where an estimated result of 10% for the 0s, 20% for the 10s, 50% for the 20s, 10% for the 30s, 5% for the 40s and 5% for the 50s is outputted as discrete quantity is shown as an example.

In the case of (a), a score is generated such that it is a fixed value for an age in a class according to the probability for each class. In the case of (b), a score is generated such that the value at the median of each class is the highest, and the larger the distance between the median and an age is, the more the score declines in a linear manner. In the case of (c), a score is generated such that it is of a normal distribution centering on the median of each class.

An example of processing of the score-generation unit 6 is shown in FIG. 6. The vertical axis of graphs in this Figure represents score of continuous quantity and the horizontal axis represents age. In the case of (a), a score may be generated such that it is a fixed value for an age within the range of ±α from an output value of the classifier 4. Also, In the case of (b), a score may be generated such that the score value of an output value of the classifier 4 is the highest, and the larger the distance between the output value and an age is, the more the score of the age declines in a linear manner. In the case of (c), a score may be generated such that it is of a normal distribution centering on an output value of the classifier 4.

The integration unit 7 integrates Sc and Sr inputted from the score-generation unit 5 and 6, respectively.

As shown in FIG. 7, the age at which score St after integration (FIG. 7 (c)) which is obtained by integrating score Sc of discrete quantity (FIG. 7 (a)) and score Sr of continuous quantity (FIG. 7 (b)) takes the peak value is outputted as an integration result.

Further, at the time of integration, weighting may be performed according to the precision of the classifiers 3 and 4. That is, when the weights of the classifiers 3 and 4 are named as Wc and Wr, respectively, score St after integration is represented as St=Wc*Sc+Wr*Sr.

Therefore, in a case where one of the classifiers 3 and 4 is more highly precise than the other, precision of estimation improves by making the weight of the more precise classifier large.

Also, the precision of estimation is improved by changing the weights for each class. For example, because the classifier 3 that handles discrete quantity is highly precise in estimation for young age groups and for old age groups, precision of age estimation increases by making the weights of these classes large. Specifically, when the weight of the classifier 3 in "the Xs" is represented with $Wc^{(X)}$, by setting $Wc^{(0)}=1.0$, $Wc^{(10)}=0.5$, $Wc^{(20)}=0.3$, $Wc^{(30)}=0.3$, $Wc^{(40)}=0.3$, $Wc^{(50)}=0.5$ and $Wc^{(60)}=1.0$, precision of age estimation for young age groups and old age groups is improved.

Although age at which score St which is obtained by integrating score Sr of continuous quantity and score Sc of discrete quantity takes the maximum value is calculated as continuous quantity, it is possible to make an output of the integration unit 7 discrete quantity. As a method to convert an output of the integration unit 7 into discrete quantity, there are a method to regard the class to which the age at which score St takes the maximum value belongs as an integration result and a method to regard the class where its area as a result of integration of score St on a class-by-class basis becomes biggest as an integration result. In an example of FIG. 8, "the 10s" in the case of the former method and "the 20s" in the case of the latter method will be outputted from the integration unit 7 as a discrete quantity of an integration result.

Although both methods may be used, the latter method is more excellent in terms of the stability of estimation accuracy.

Thus, because an age estimation system according to this exemplary embodiment integrates an estimated result obtained as a discrete quantity and an estimated result obtained as a continuous quantity, there are no cases that precision of estimation of a specific age group becomes low.

Moreover, by integrating a score based on an estimated result obtained as a discrete quantity and a score based on an estimated result obtained as a continuous quantity giving weight to them, it is possible to improve the estimation accuracy further. In this case, the precision of estimation can be made higher by changing the weight according to a class.

The Second Exemplary Embodiment

The second exemplary embodiment in which the present invention is implemented suitably will be described.

The structure of an age estimation system according to this exemplary embodiment is shown in FIG. 9. Although it is a structure almost similar to that of the first exemplary embodiment, the score-generation units 5 and 6 can refer to criterion data which each of the classifiers 3 and 4 uses for estimation of age.

Processing of the feature extraction units 1 and 2, and the integration unit 7 are the same as that of the first exemplary embodiment.

In this exemplary embodiment, the score-generation unit 5 generates a score of an estimated result with reference to criterion data of the classifier 3. When age information is included in criterion data used for learning as a parameter, the distribution of age information of a person estimated to belong to a specific age group can be extracted by performing a reverse lookup of the criterion data of the classifier 3. Therefore, the score-generation unit 5 extracts data which should be estimated to be a specific age group from the criterion data of the classifier 3 and outputs its distribution as a score of the age group as shown in FIG. 10(a).

Similarly, the score-generation unit 6 generates a score of an estimated result with reference to the criterion data of the classifier 4. When age information is included in criterion data used for learning as a parameter, the age information of a person estimated to belong to a specific age group can be extracted by performing a reverse lookup of the criterion data of the classifier 4. Therefore, the score-generation unit 6 extracts data which should be estimated to be in a range of ±α from a specific age from the criterion data of the classifier 4 and outputs its distribution as a score of the age as shown in FIG. 10(b).

Age information of a person estimated to be in a certain age group may not be symmetrical distribution about the median of the age group. For example, the distribution of age information of persons estimated to be in their 20s generally becomes higher than the age of 25 which is the median, because there are more cases in which a person in his/her 30s, an age group in which specific features do not appear easily, is estimated as in his/her 20s than cases in which a person in his/her 10s, an age group in which specific features appear easily, is estimated as in his/her 20s. This is also similar in the case of continuous quantity, and age information of persons estimated to be in a certain age may not be symmetrical distribution about the age.

In this exemplary embodiment, it is possible to estimate age more correctly, because a score for a discrete quantity and a continuous quantity is generated using criterion data used for estimation of age.

The score for a discrete quantity and a continuous quantity are integrated in the integration unit 7 like the first exemplary embodiment as shown in FIG. 10 (c), and an integration result is outputted as a discrete quantity or a continuous quantity.

Further, although a case in which a score is generated based on criterion data used by the classifiers 3 and 4 for estimation of age has been described here, when there is measured data (including the relation between age information and an estimated result) which the classifiers 3 and 4 have not learned, the score-generation units 5 and 6 may perform process of generating a score based on that, as shown in FIG. 11.

The Third Exemplary Embodiment

The third exemplary embodiment in which the present invention is implemented suitably will be described.

The structure of an age estimation system according to this exemplary embodiment is shown in FIG. 12. In this exemplary embodiment, there are provided two classifiers (4a and 4b) which estimate age of a person as a continuous quantity, and feature quantities A and B extracted by the feature extraction unit 2 are inputted separately.

Note that, the feature extraction unit 1, the classifier 3 and the score-generation unit 5 correspond to the first estimation unit 51 in FIG. 1. The feature extraction unit 2, the classifiers 4a, 4b and the score-generation unit 6 correspond to the second estimation unit 52 in FIG. 1. The integration unit 7 corresponds to the integration unit 53 in FIG. 1.

The score-generation unit 6 outputs score Sr of continuous quantity based on estimated results inputted from classifiers 4a and 4b, respectively.

An example of processing of the score-generation unit 6 is shown in FIG. 13. The score-generation unit 6 combines a score based on an estimated result inputted from the classifier 4a (FIG. 13 (*a*)) and a score based on an estimated result inputted from the classifier 4b (FIG. 13 (*b*)), and calculates score Sr (FIG. 13 (*c*)) of continuous quantity.

The score of combined continuous quantity is integrated with the score of the discrete quantity in the integration unit 7 like the first exemplary embodiment, and an integration result is outputted from the integration unit 7 as a discrete quantity or a continuous quantity.

Thus, by generating a score by combining estimated results which are outputted from a plurality of classifiers, a measurement error is reduced and the estimation accuracy is improved.

Meanwhile, although the structure in which the feature extraction unit 2 extracts two feature quantities to input to the separate classifier 4a and 4b has been described as an example here, a plurality of feature extraction units themselves may be provided as shown in FIG. 14, or a same feature may be inputted to separate classifiers as shown in FIG. 15. When a same feature is inputted to different classifiers, the similar effect is obtained, because when learned pieces of criterion data are different, outputted estimated results are different.

Although the case where estimated results of two classifiers are combined has been described as an example here, it is needless to say that the structure may be such that estimated results of classifiers of no smaller than 3 are combined.

The Fourth Exemplary Embodiment

The fourth exemplary embodiment in which the present invention is implemented suitably will be described.

The structure of an age estimation system according to this exemplary embodiment is shown in FIG. 16. In this exemplary embodiment, there are provided two classifiers (3a and 3b) which estimate age of a person as a discrete quantity, and feature quantities C and D extracted by the feature extraction unit 1 are inputted separately.

Note that, the feature extraction unit 1, the classifiers 3a, 3b and the score-generation unit 5 correspond to the first estimation unit 51 in FIG. 1. The feature extraction unit 2, the classifier 4 and the score-generation unit 6 correspond to the second estimation unit 52 in FIG. 1. The integration unit 7 corresponds to the integration unit 53 in FIG. 1.

The score-generation unit 5 outputs score Sc of discrete quantity based on estimated results inputted from classifiers 3a and 3b, respectively.

Because it is the same as that of the third exemplary embodiment except that the target of combining is a score of discrete quantity, the overlapped description will be omitted.

The Fifth Exemplary Embodiment

The fifth exemplary embodiment in which the present invention is implemented suitably will be described.

The structure of an age estimation system according to this exemplary embodiment is shown in FIG. 17. This system includes the feature extraction units 11, 12, 21 and 22, classifiers 13, 14, 23 and 24, score-generation units 15, 16, 25 and 26, and an integration unit 17.

A first input image is inputted to the feature extraction units 11 and 12, and a second input image is inputted to the feature extraction units 21 and 22. The feature extraction units 11 and 21 are similar to the feature extraction unit 1 of the first exemplary embodiment, the feature extraction units 12 and 22 to the feature extraction unit 2 of the first exemplary embodiment, the classifiers 13 and 23 to the classifier 3 of the first exemplary embodiment, the classifiers 14 and 24 to the classifier 4 of the first exemplary embodiment, the score-generating units 15 and 25 to the score-generating unit 5 of the first exemplary embodiment, the score-generating units 16 and 26 to the score-generating unit 6 of the first exemplary embodiment and the integration unit 17 to the integration unit 7 of the first exemplary embodiment, respectively.

An age estimation system according to this exemplary embodiment calculates score Sc1 of discrete quantity and Sr1 of continuous quantity based on an input image 1, and score Sc2 of discrete quantity and Sr2 of continuous quantity based on an input image 2 separately, and obtains an estimated result by integrating these.

Because processing in each part is the same as that of each of the above-mentioned exemplary embodiments, the description will be omitted.

Because an age estimation system according to this exemplary embodiment estimates age based on a plurality of images, even when shooting condition of any one of images is bad and a feature cannot be extracted well, age can be estimated from the other images, and thus, precision of age estimation becomes high.

Although a case where there are two input images has been described, by arranging a structure such that the number of input images, and the number of pairs of a processing system which estimates an age as a discrete quantity and a processing system which estimates an age as a continuous quantity are the same, even when the number of input images is 3 or more, it is possible to improve estimation accuracy by integrating estimated results which are made based on each input image like the above-mentioned example.

Further, each of the above-mentioned exemplary embodiments is an example of suitable implementation of the present invention, and the present invention is not limited to this.

For example, in each of the above-mentioned exemplary embodiments, although a case where the age of a person is estimated based on an input image has been described as an example, the gender of a person may be estimated instead of the age. In this case, by digitizing the gender of a woman as '1' and a man as '0', it can be estimated as a discrete quantity and a continuous quantity like the case of age. As shown in FIG. 18, by performing the same processing as each of the above-mentioned exemplary embodiments in parallel, the age and the gender of a person may be estimated simultaneously.

Data which is used as the base of estimation is not limited to an image, and it may be voice and the like, and it may be a combination of data of no smaller than two kinds of form (voice+image, for example).

Thus, various modifications of the present invention are possible.

This application claims priority based on Japanese application Japanese Patent Application No. 2007-254295 filed on Sep. 28, 2007, the disclosure of which is incorporated herein in its entirety.

Figure 1:
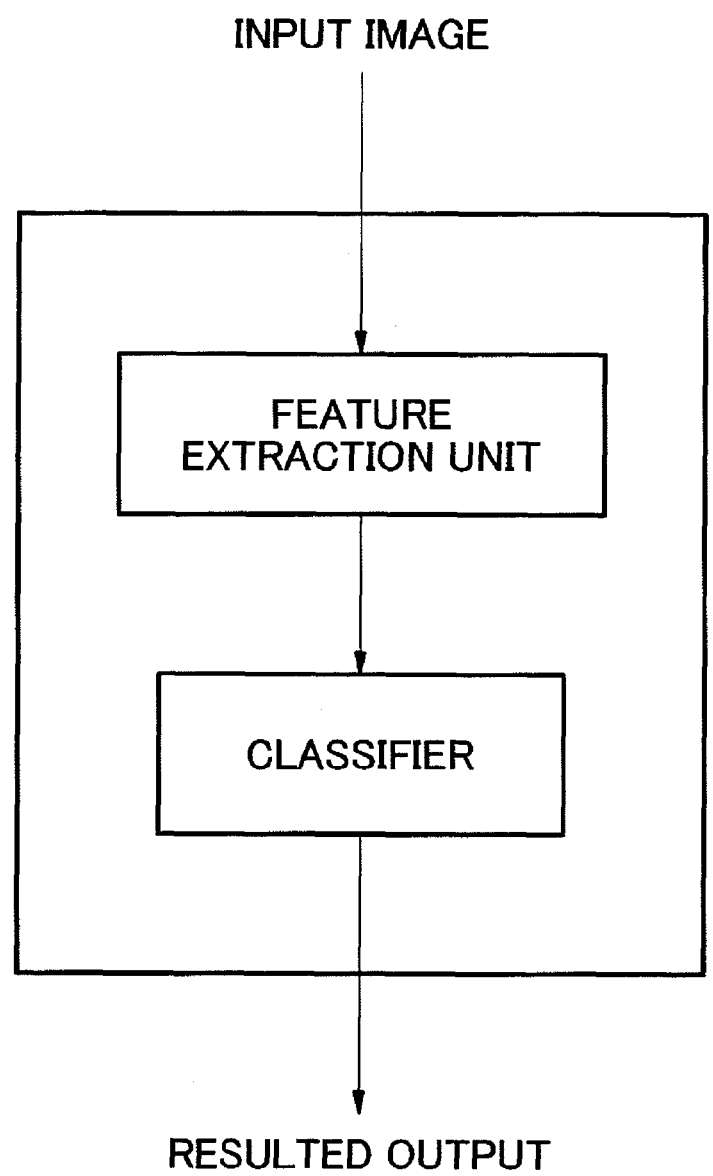
FIG. 1 is a diagram showing a structure of an age estimation system related to the present invention.
Figure 2:
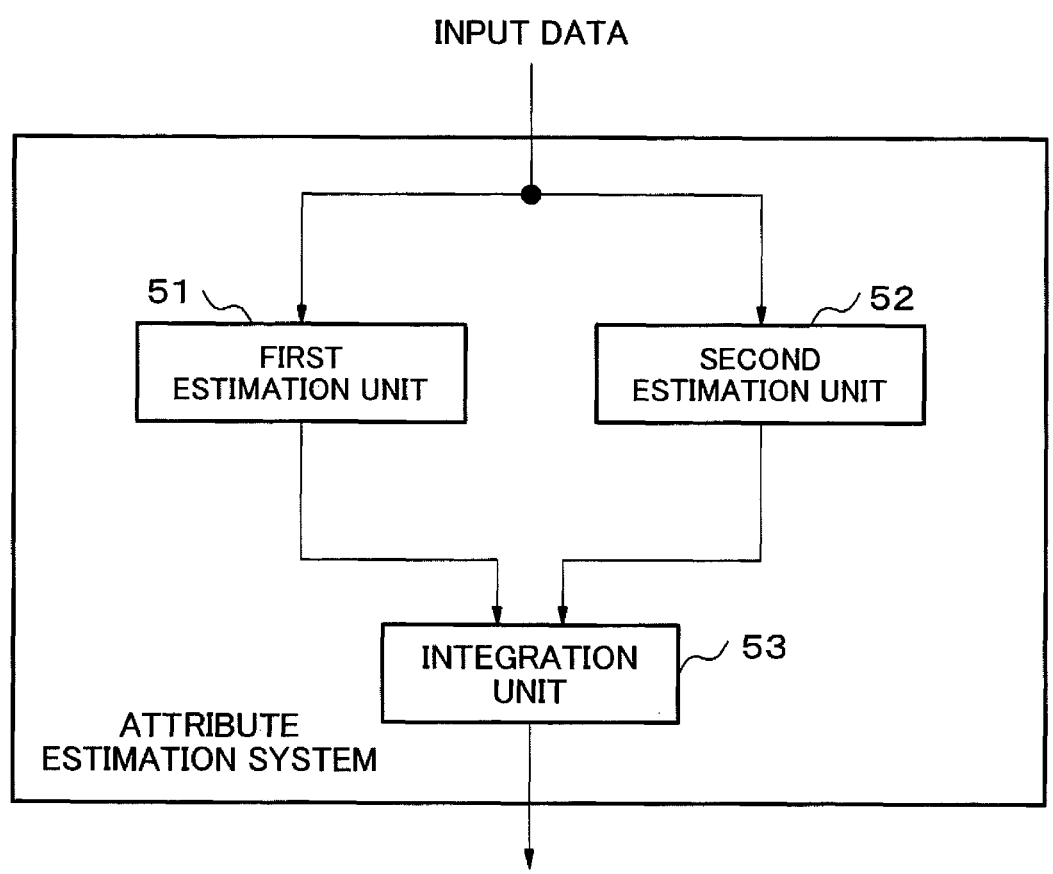
FIG. 2 is a diagram showing a structure of an attribute estimation system according to the present invention.
Figure 3:
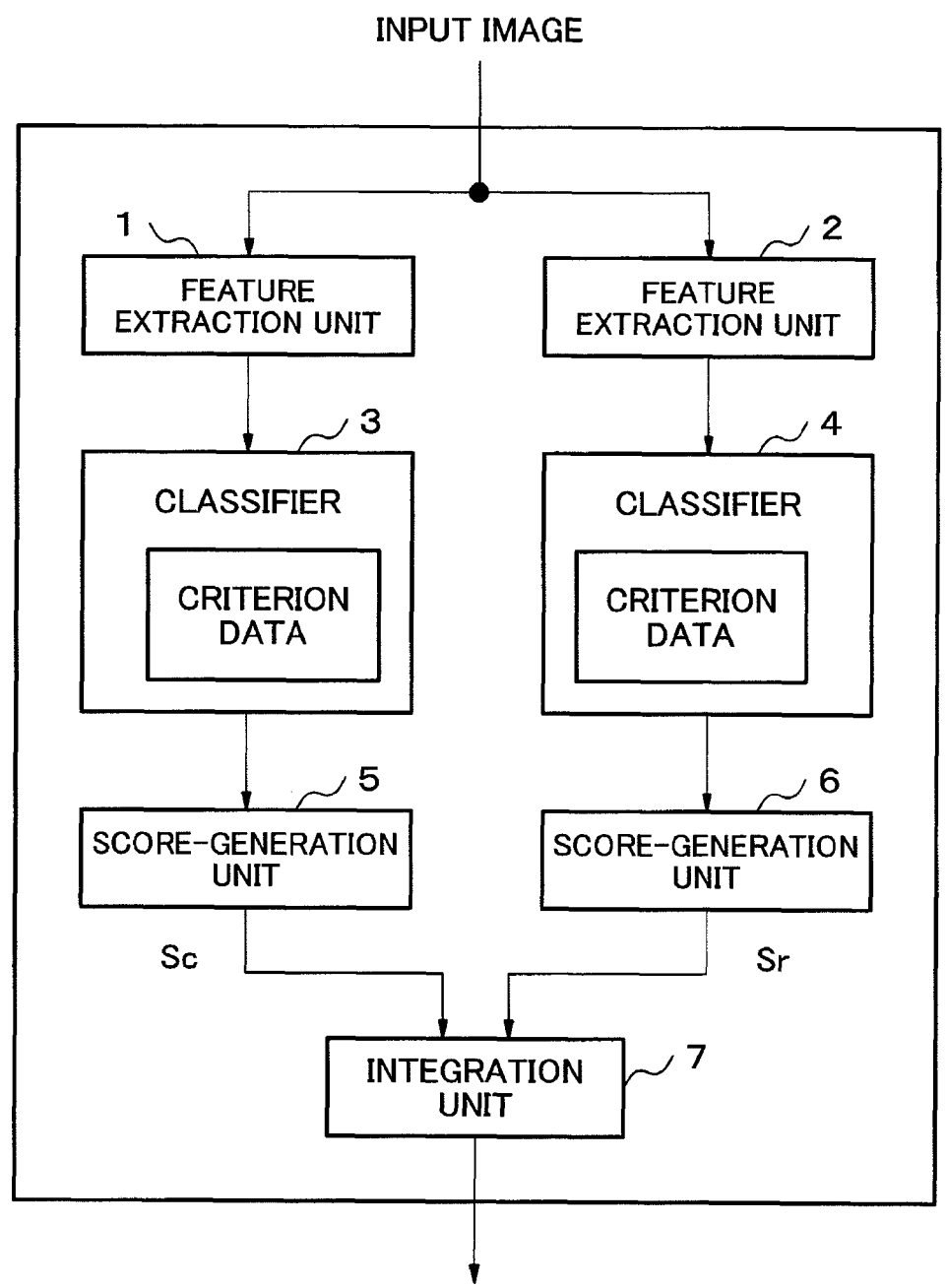
FIG. 3 is a diagram showing a structure of an age estimation system according to the first exemplary embodiment in which the present invention is implemented suitably.
Figure 4A:
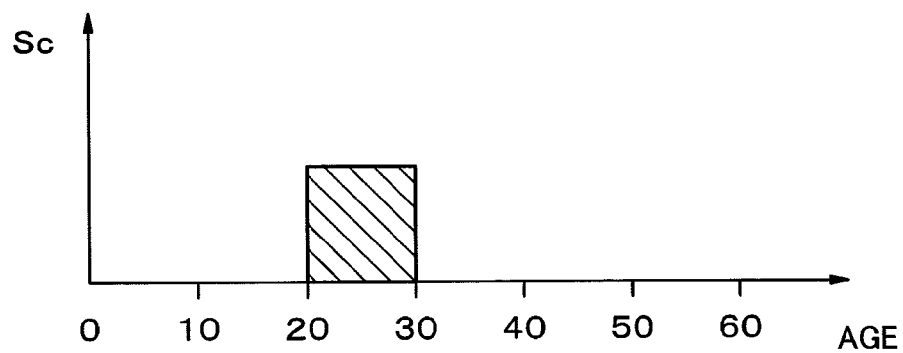
FIG. 4A is a diagram showing a first exemplary embodiment of generating a score of discrete quantity.
Figure 4B:
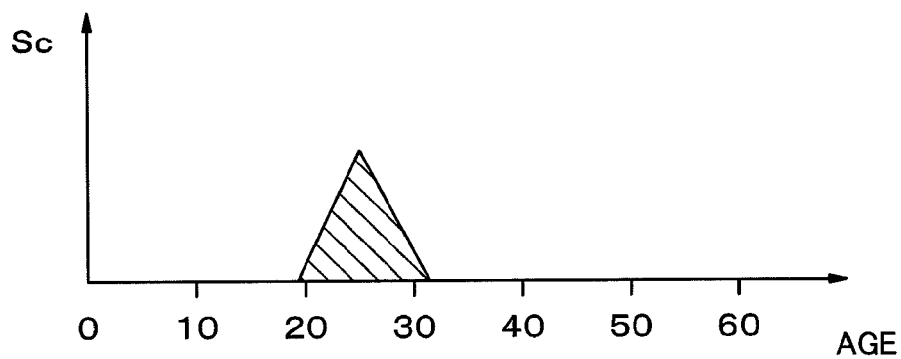
FIG. 4B is a diagram showing a second exemplary embodiment of generating a score of discrete quantity.
Figure 4C:
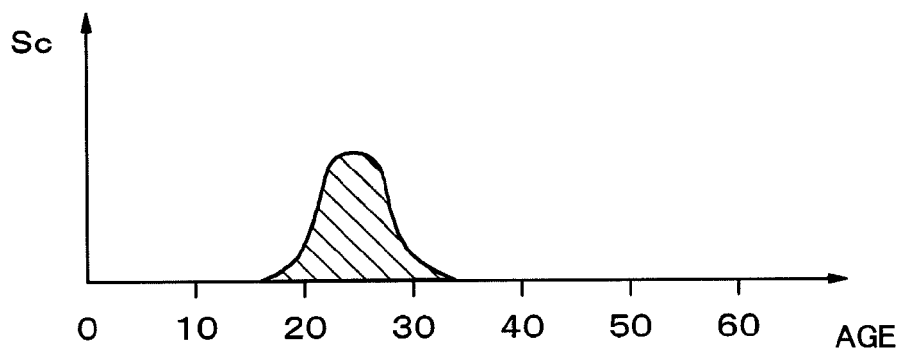
FIG. 4C is a diagram showing a third exemplary embodiment of generating a score of discrete quantity.
Figure 5A:
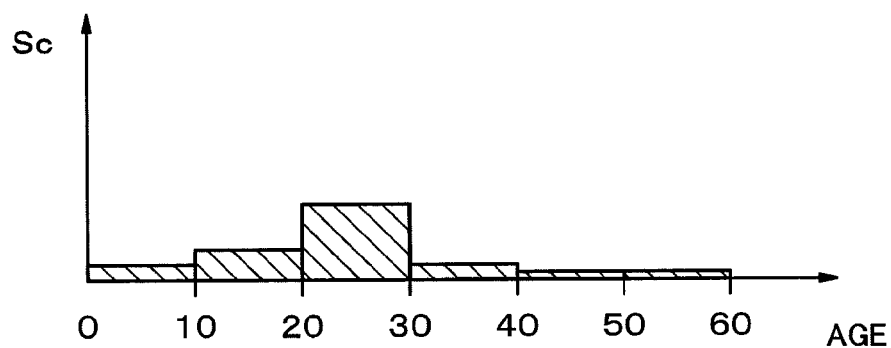
FIG. 5A is a diagram showing a first exemplary embodiment of generating a score of discrete quantity.
Figure 5B:
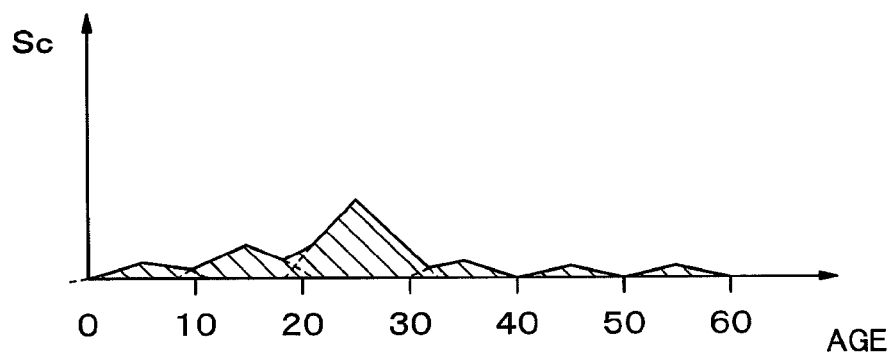
FIG. 5B is a diagram showing a second exemplary embodiment of generating a score of discrete quantity.
Figure 5C:
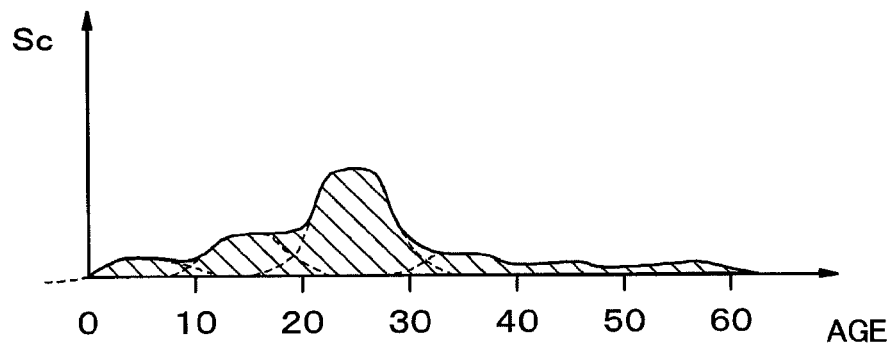
FIG. 5C is a diagram showing a third exemplary embodiment of generating a score of discrete quantity.
Figure 6A:
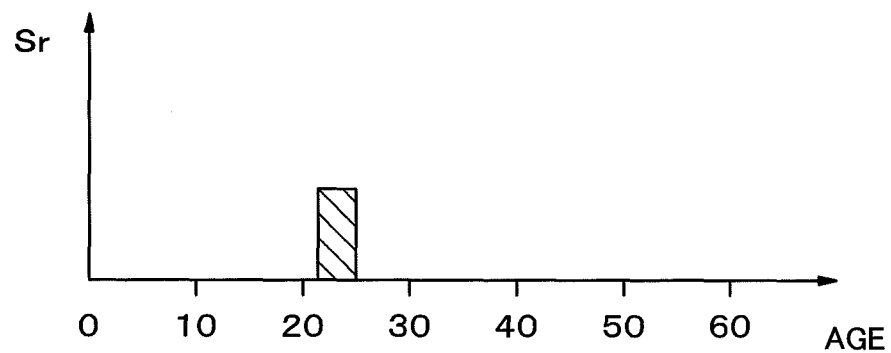
FIG. 6A is a diagram showing a first exemplary embodiment of generating a score of continuous quantity.
Figure 6B:
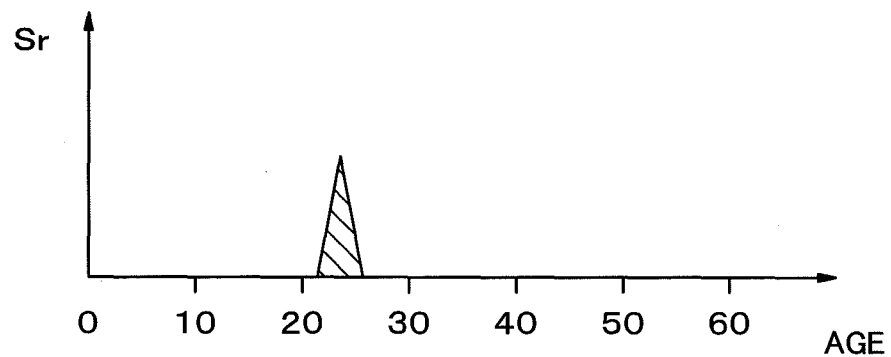
FIG. 6B is a diagram showing a second exemplary embodiment of generating a score of continuous quantity.
Figure 6C:
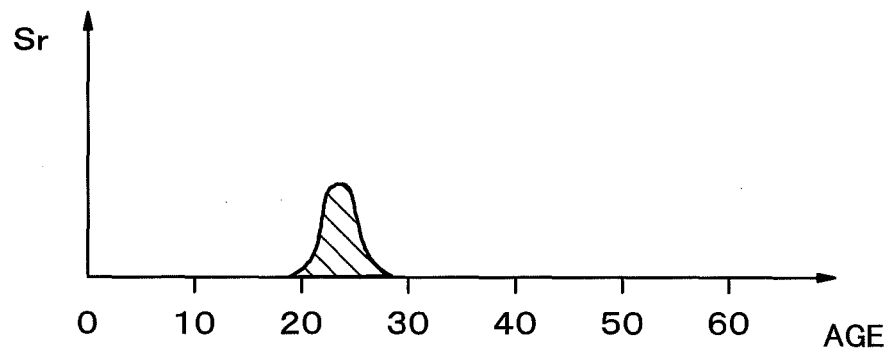
FIG. 6C is a diagram showing a third exemplary embodiment of generating a score of continuous quantity.
Figure 7A:
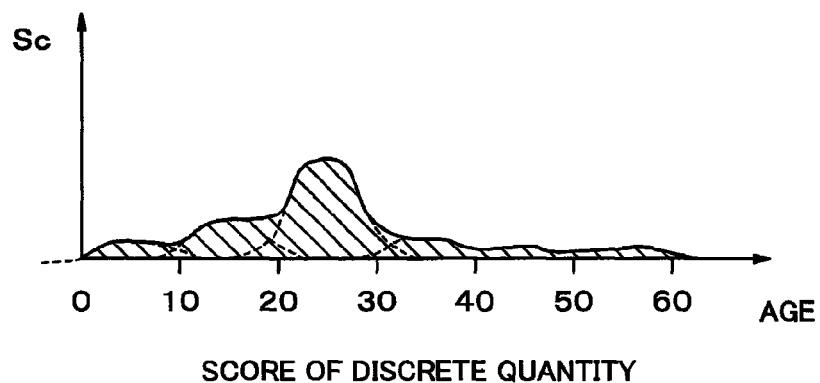
FIG. 7A is a diagram showing a first exemplary embodiment of integration of a score of discrete quantity and a score
Figure 7B:
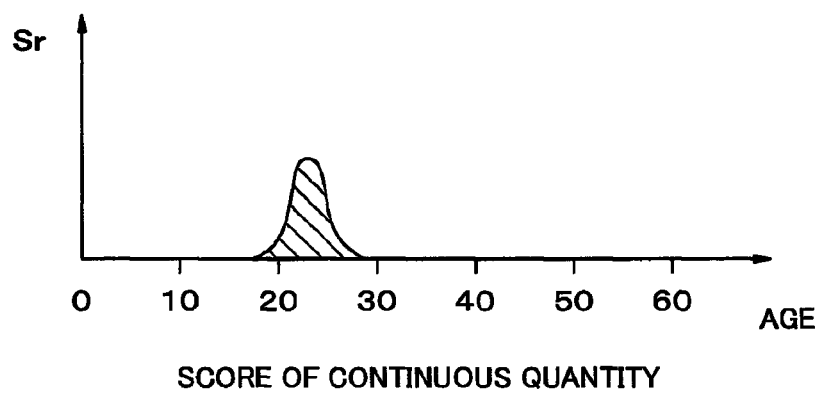
FIG. 7B is a diagram showing a second exemplary embodiment of integration of a score of discrete quantity and a score
Figure 7C:
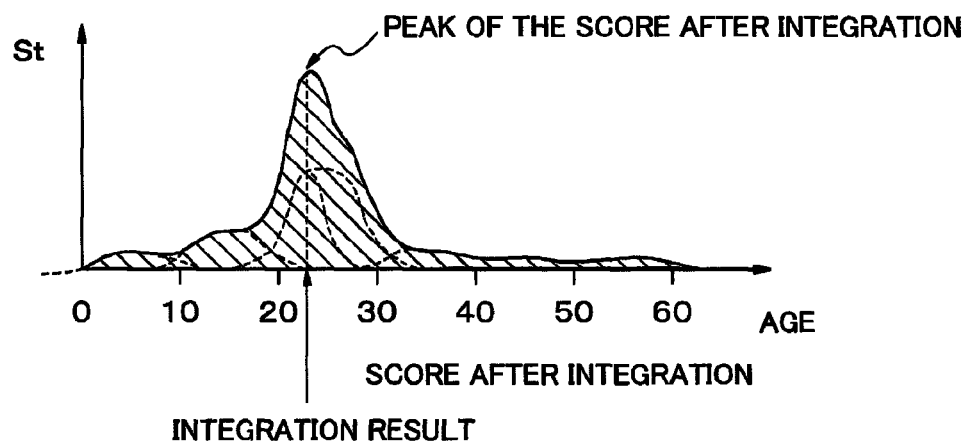
FIG. 7C is a diagram showing a third exemplary embodiment of integration of a score of discrete quantity and a score of continuous quantity.
Figure 8:
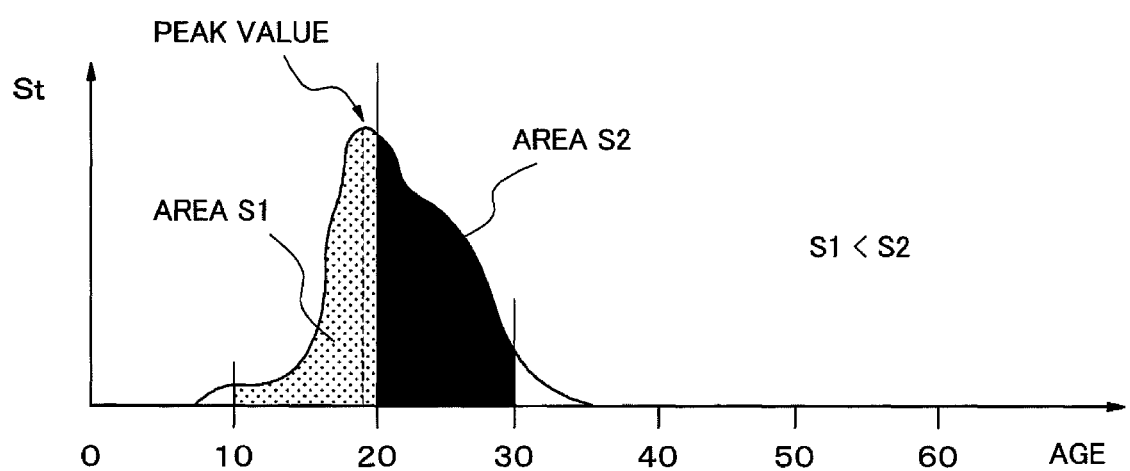
FIG. 8 is a diagram showing an example of processing in which an integration result is changed into a discrete quantity.
Figure 9:
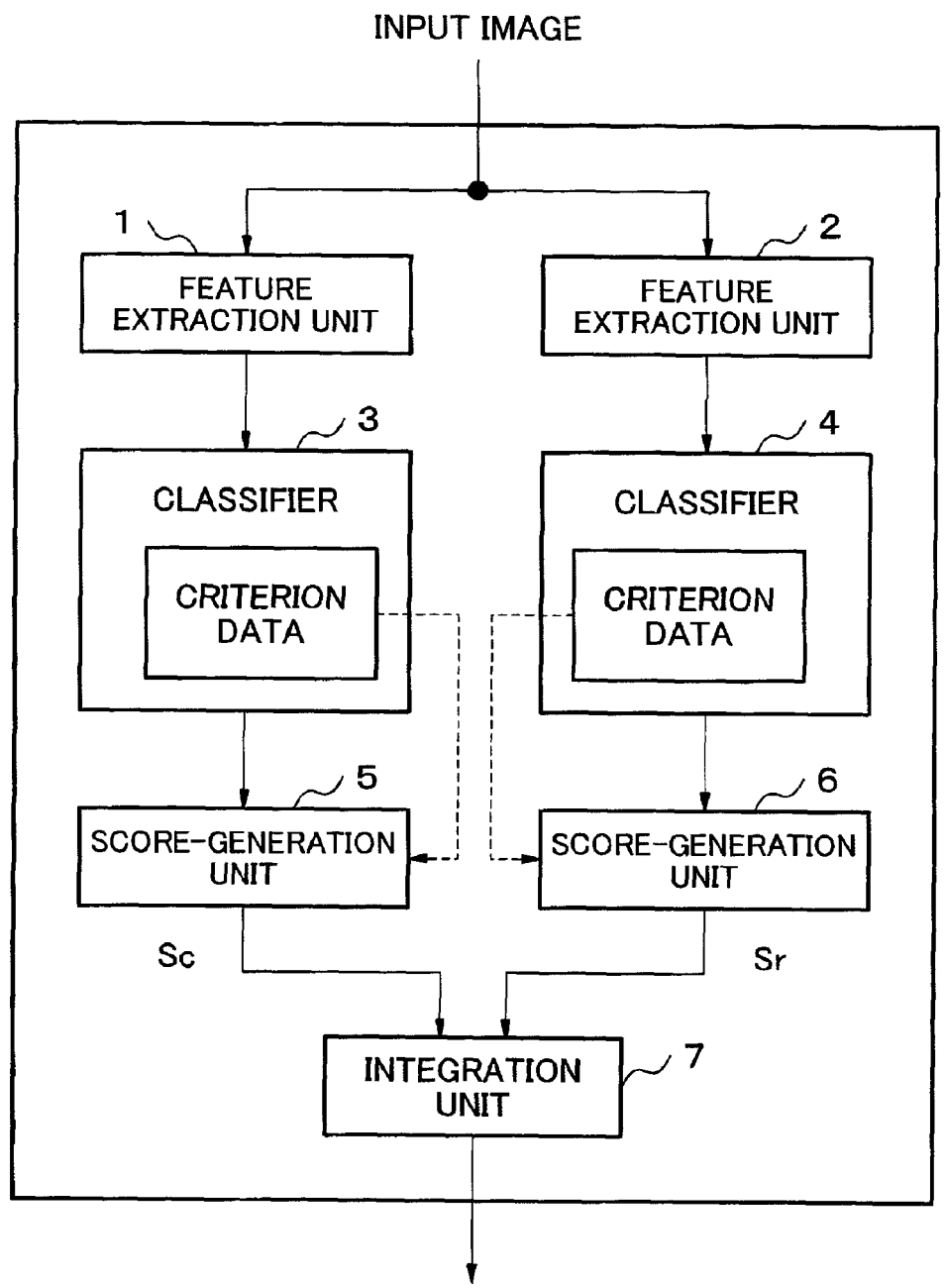
FIG. 9 is a diagram showing a structure of an age estimation system according to the second exemplary embodiment in which the present invention is implemented suitably.
Figure 10A:
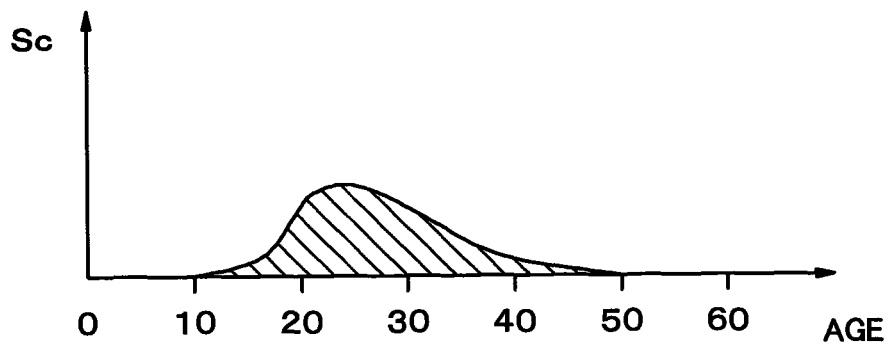
FIG. 10A is a diagram showing a first exemplary embodiment of generating a score using criterion data.
Figure 10B:
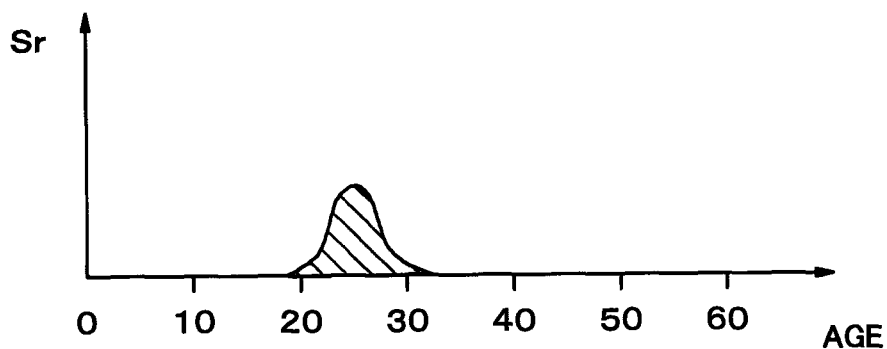
FIG. 10B is a diagram showing a second exemplary embodiment of generating a score using criterion data.
Figure 10C:
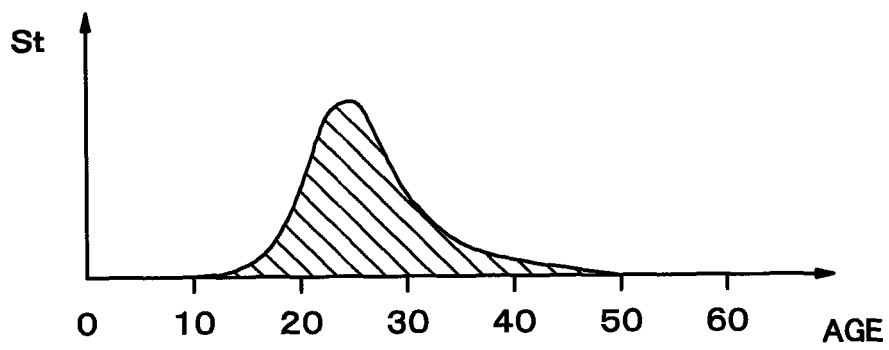
FIG. 10C is a diagram showing a third exemplary embodiment of generating a score using criterion data.
Figure 11:
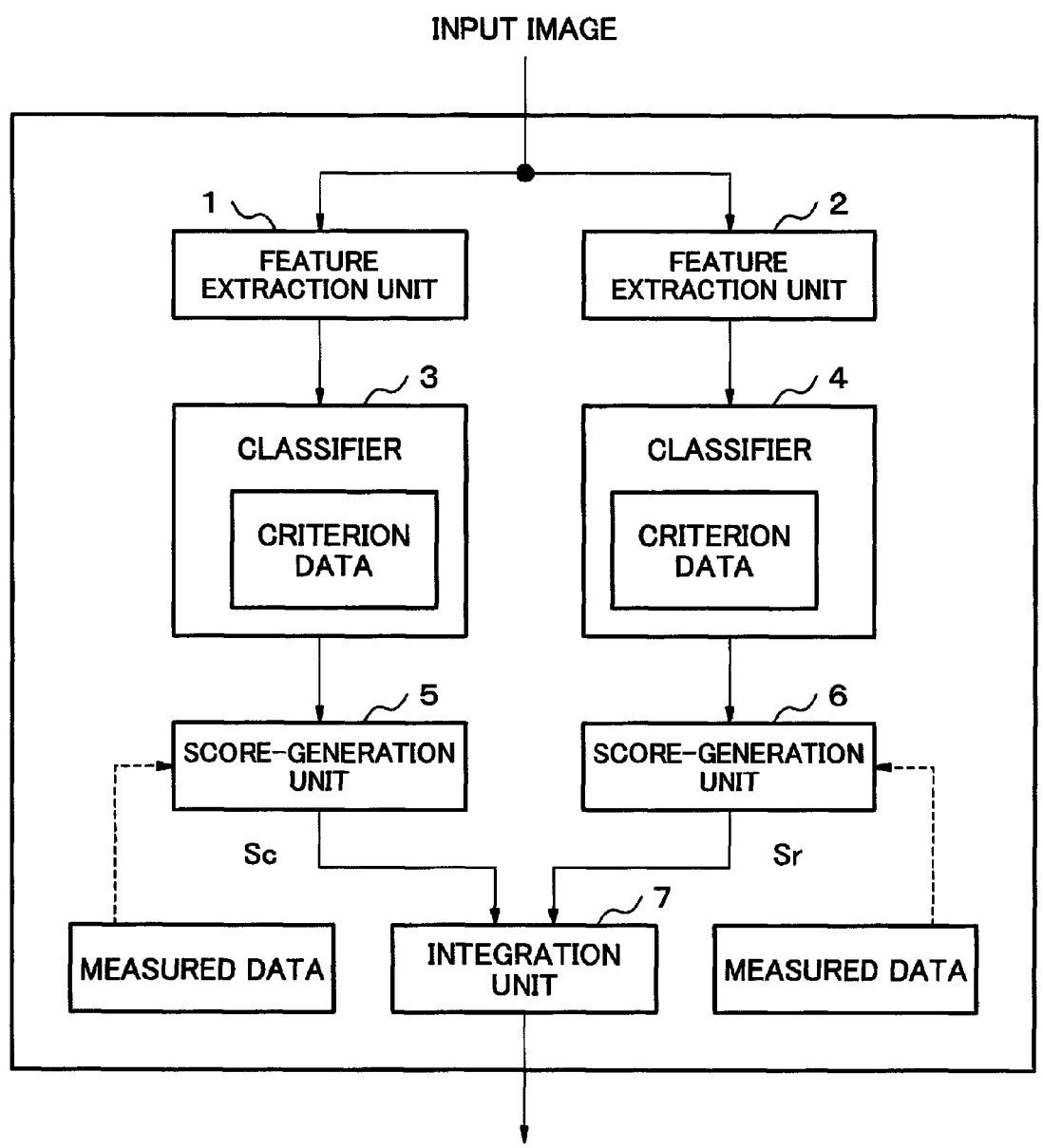
FIG. 11 is a diagram showing an exemplary configuration of a system which generates a score based on measured data which has not been learned by a classifier yet.
Figure 12:
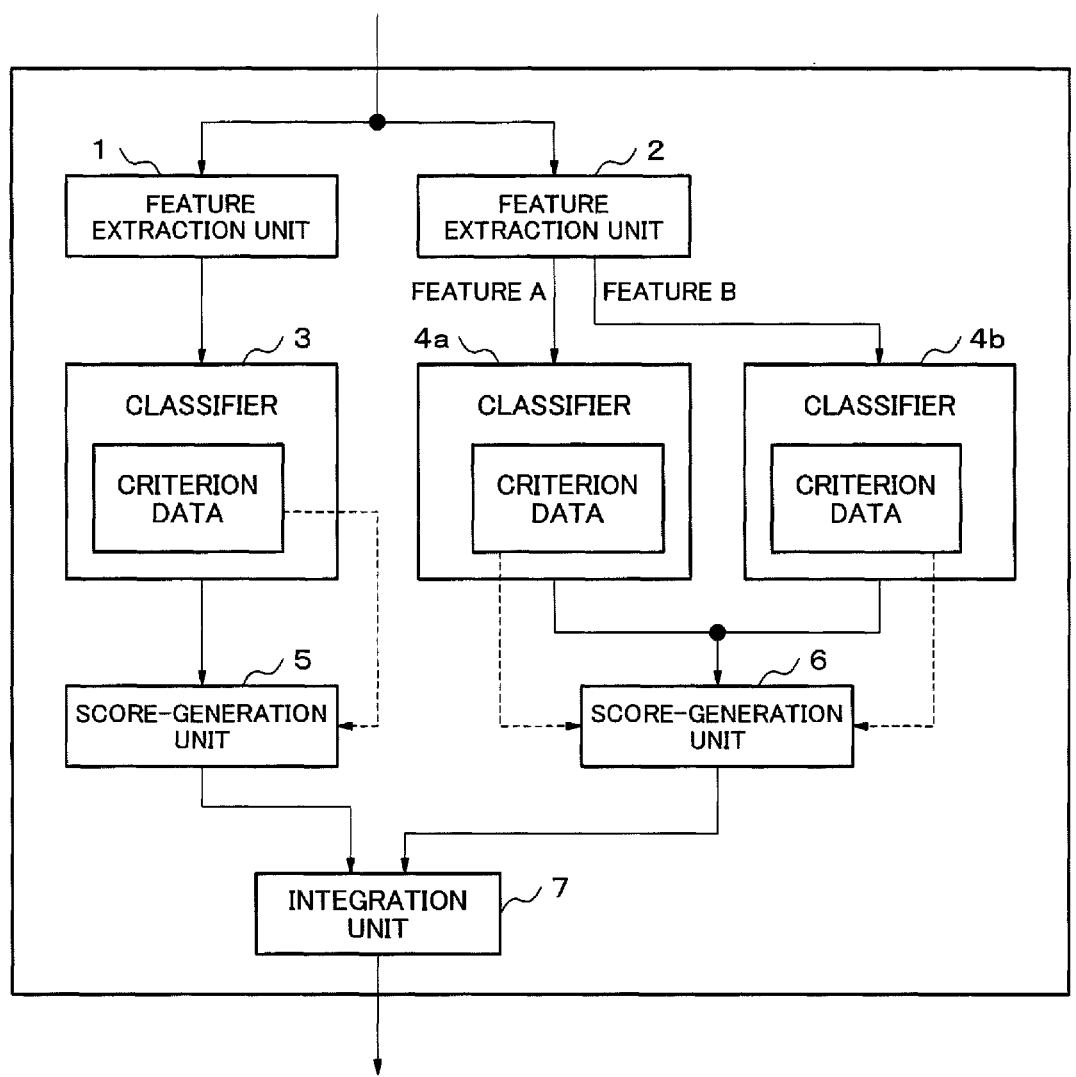
FIG. 12 is a diagram showing a structure of an age estimation system according to the third exemplary embodiment in which the present invention is implemented suitably.
Figure 13A:
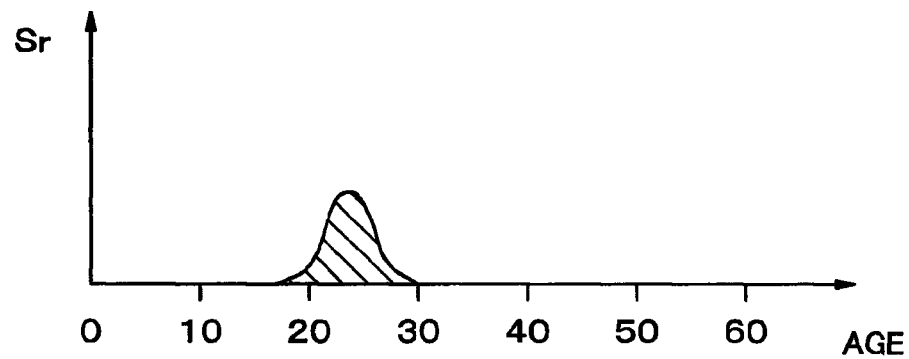
FIG. 13A is a diagram showing a first exemplary embodiment of processing in which scores from estimated results of a plurality of classifiers are combined.
Figure 13B:
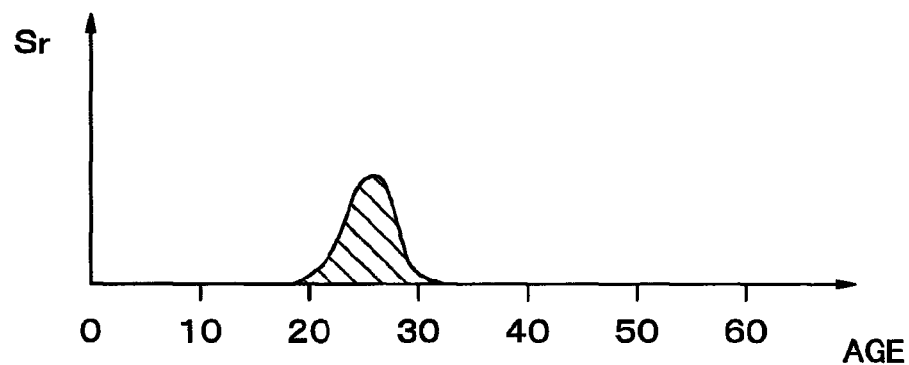
FIG. 13B is a diagram showing a second exemplary embodiment of processing in which scores from estimated results of a plurality of classifiers are combined.
Figure 13C:
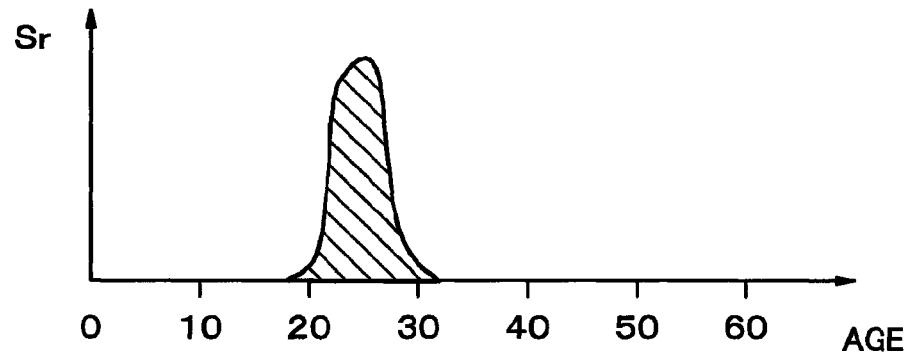
FIG. 13C is a diagram showing a third exemplary embodiment of processing in which scores from estimated results of a plurality of classifiers are combined.
Figure 14:
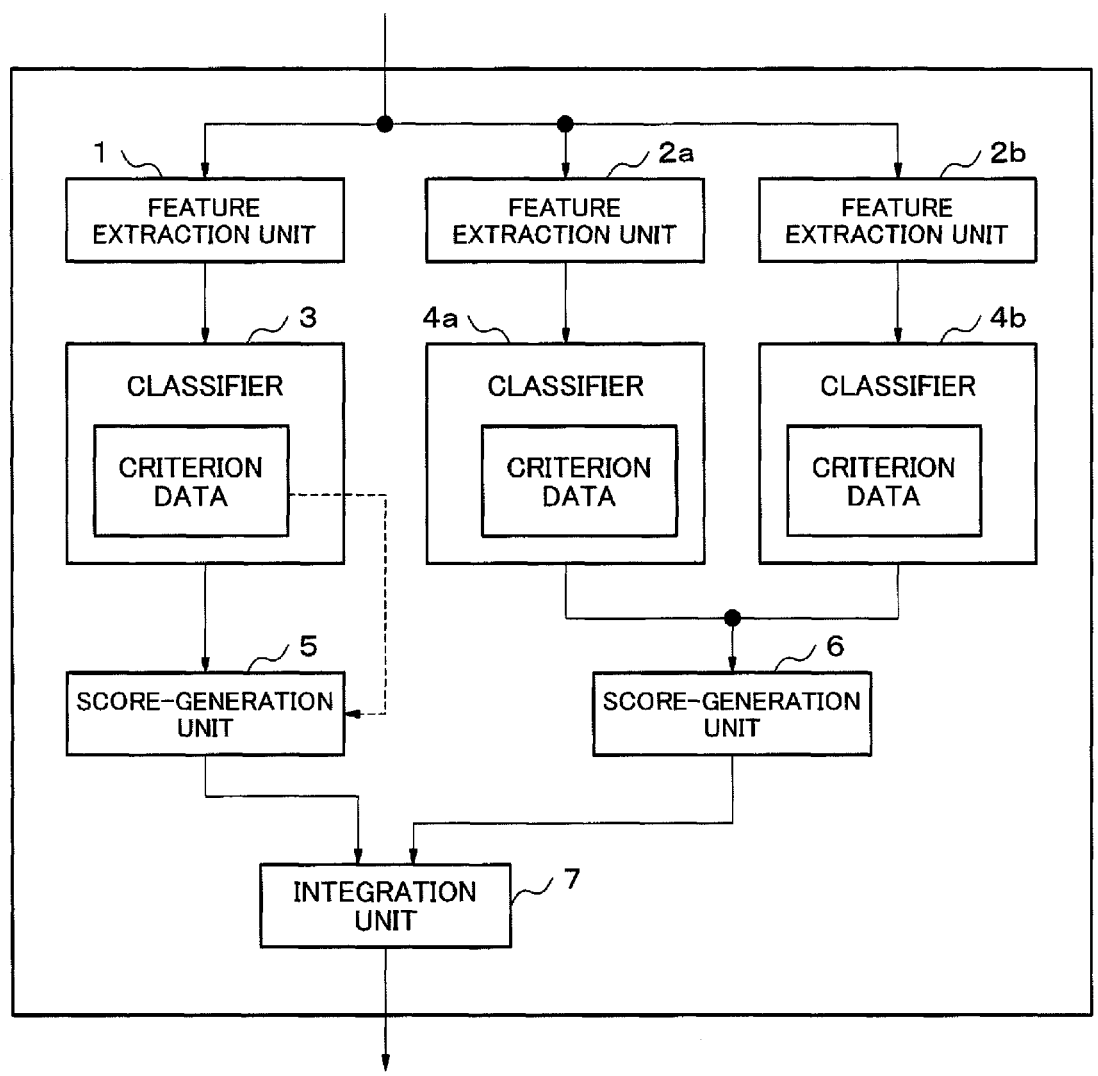
FIG. 14 is a diagram showing a different structure of an age estimation system according to the third exemplary embodiment.
Figure 15:
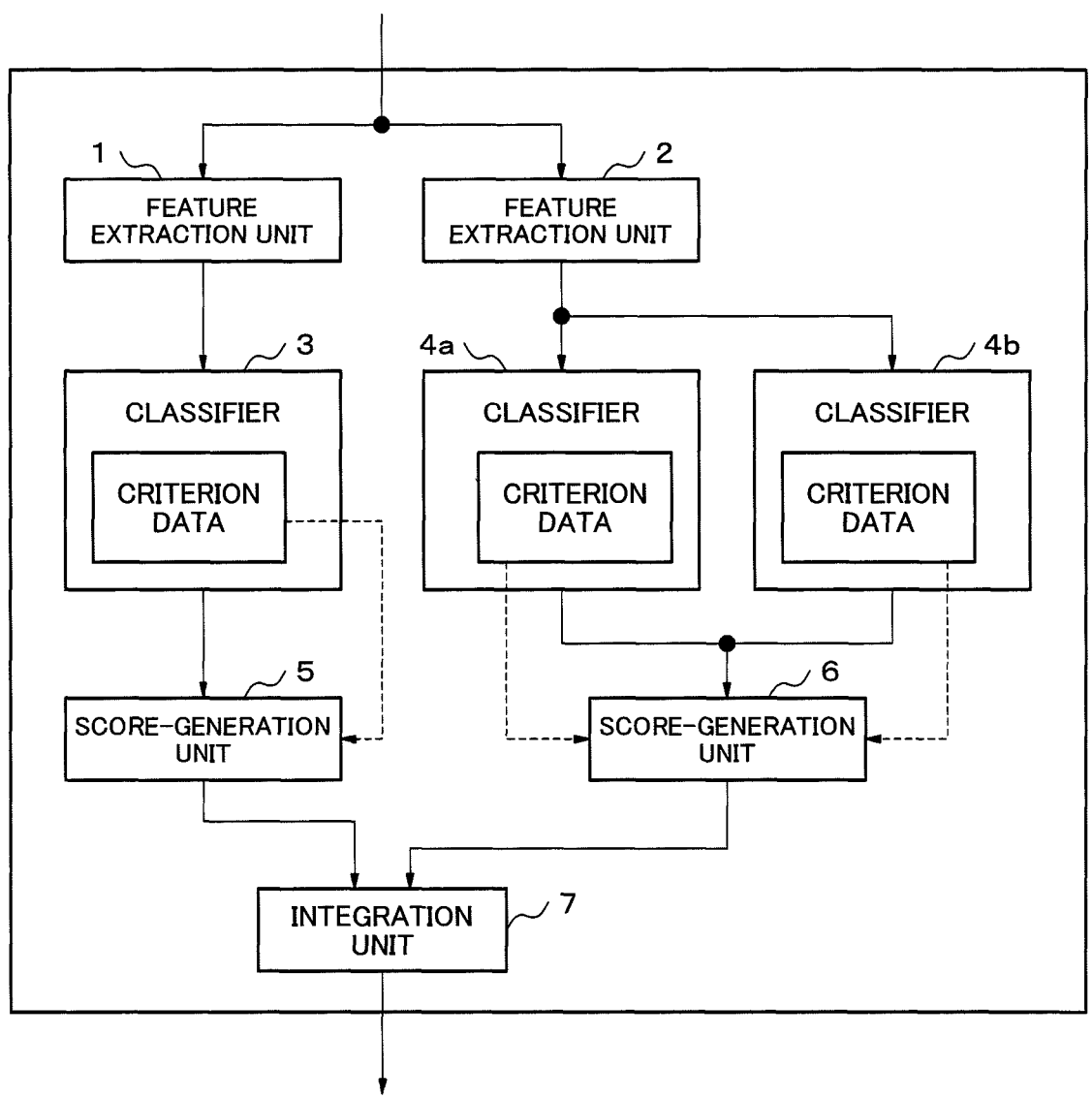
FIG. 15 is a diagram showing a different structure of an age estimation system according to the third exemplary embodiment.
Figure 16:
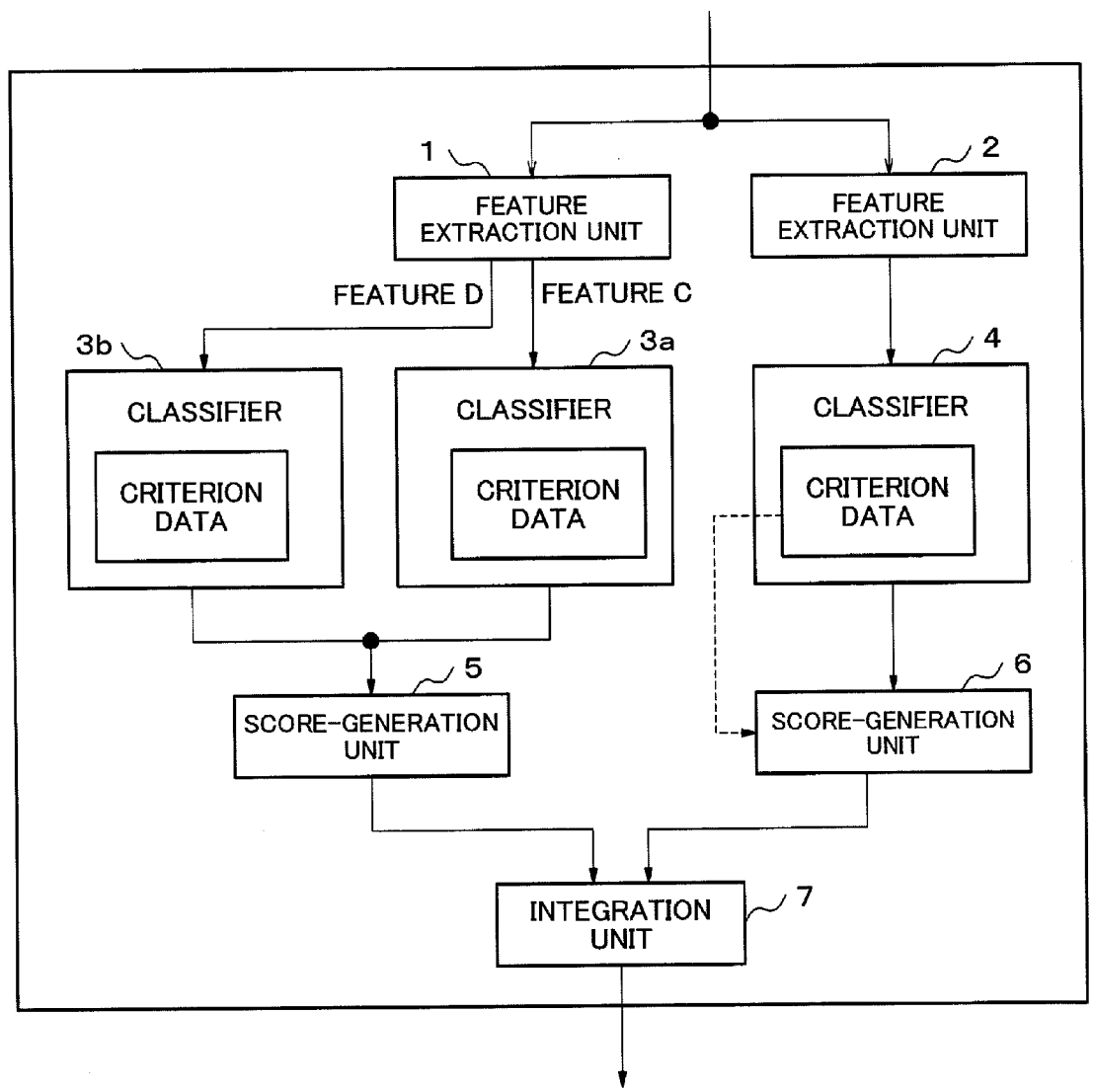
FIG. 16 is a diagram showing a structure of an age estimation system according to the fourth exemplary embodiment in which the present invention is implemented suitably.
Figure 17:
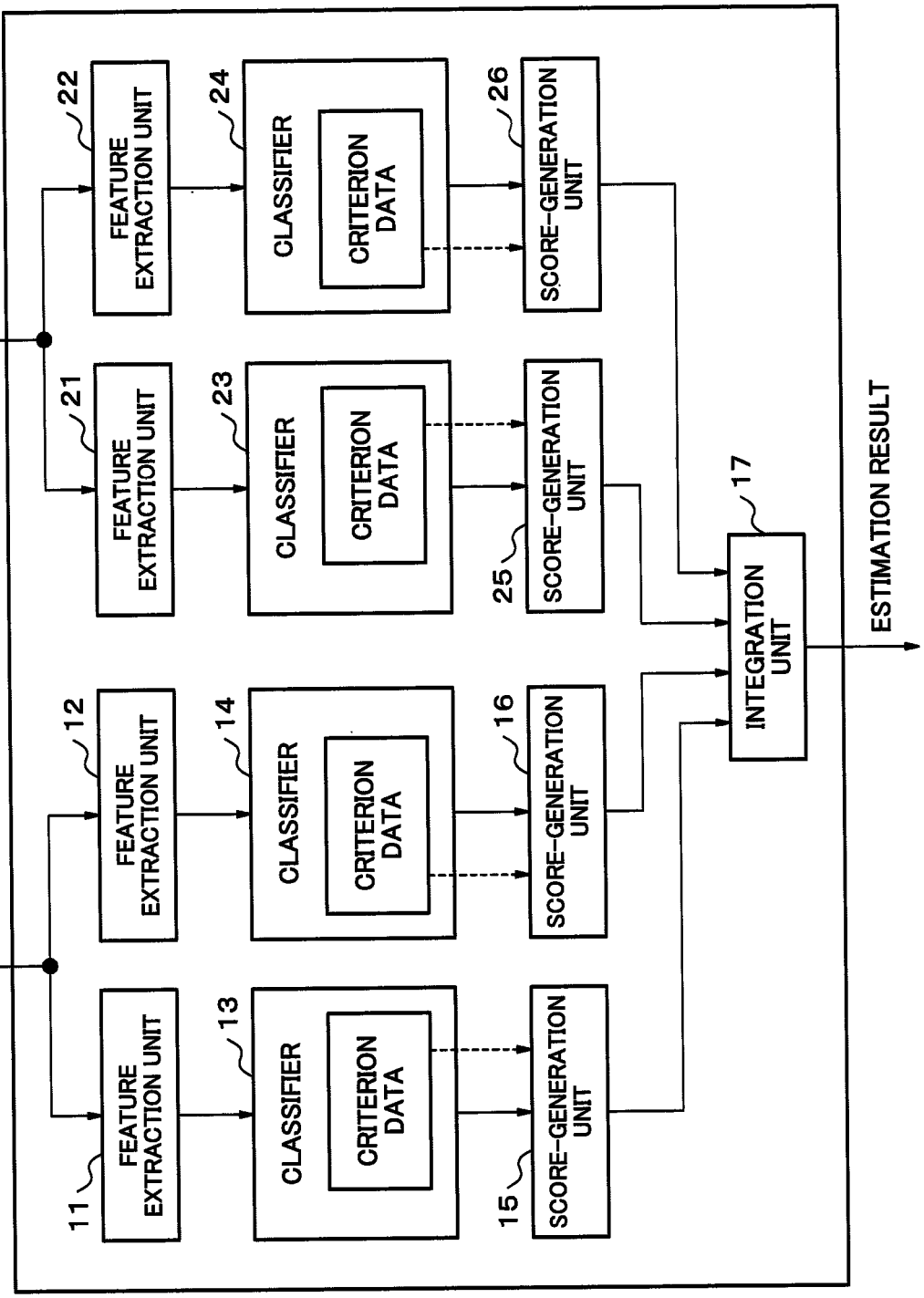
FIG. 17 is a diagram showing a structure of an age estimation system according to the fifth exemplary embodiment in which the present invention is implemented suitably.
Figure 18:
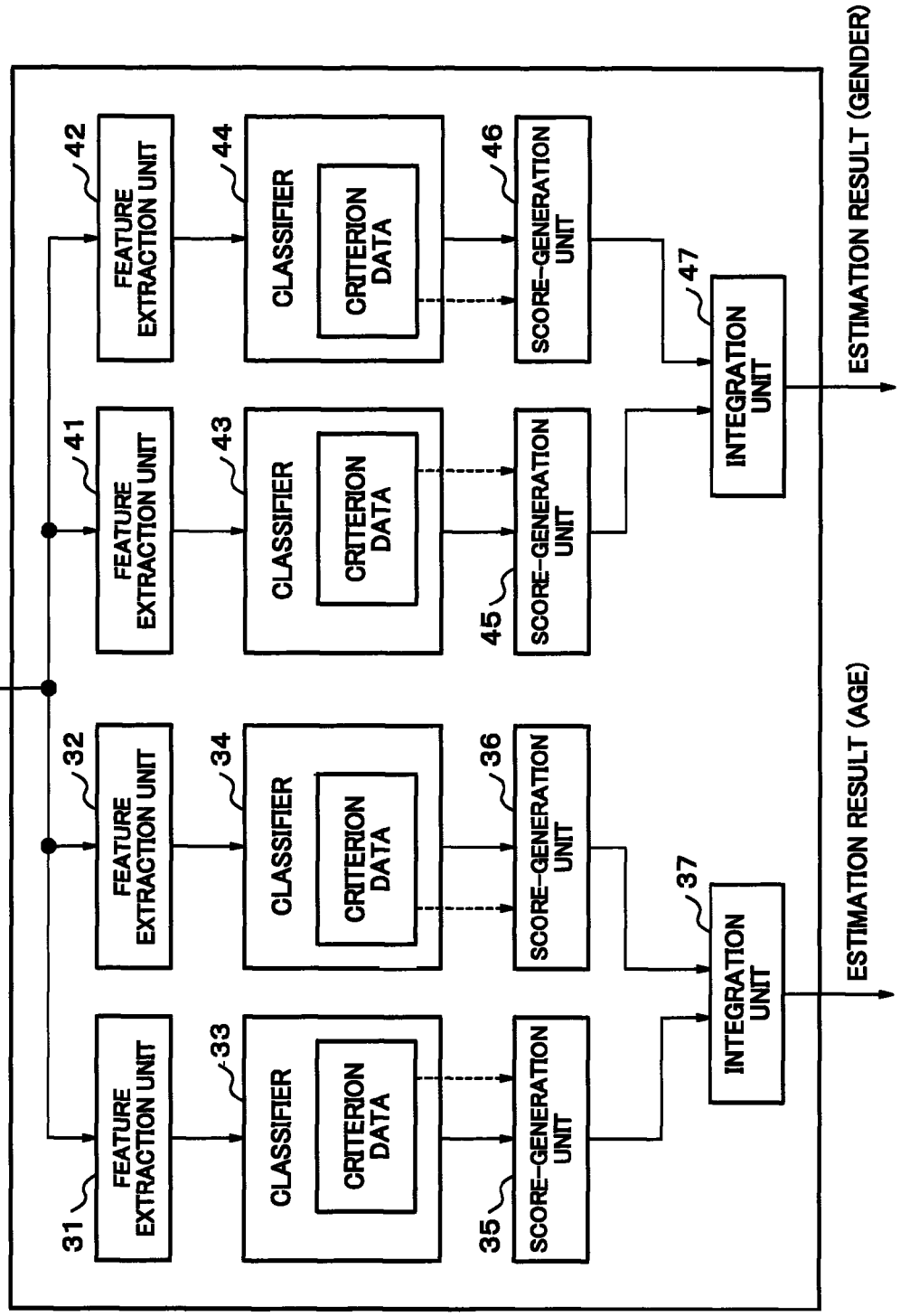
FIG. 18 is a diagram showing a structure of a system to estimate gender as well as age.

DESCRIPTION OF THE NUMERALS 1, 2, 11, 12, 21, 22, 31, 32, 41, 42 Feature extraction unit;
3, 4, 13, 14, 23, 24, 33, 34, 43 and 44 Discrimination unit;
5, 6, 15 16, 25 and 26 Score-generation unit;
7, 17, 37, 47 and 53 Integration unit;
51 First estimation unit; and
52 Second estimation unit

The invention claimed is:

1. An age estimation system, having a processor, and a memory storing instructions to be executed by the processor, that estimates an age based on at least one piece of input data, wherein the ages are separated into a plurality of classes, each indicating a predetermined age group, the system comprising:

a first estimation unit which includes at least one first feature extraction unit which extracts at least one first feature from said input data, and which estimates said age as a discrete quantity based on said first feature;

a second estimation unit which includes at least one second feature extraction unit which extracts at least one second feature from said input data, and which estimates said age as a continuous quantity based on said second feature;

a score-generation unit which generates a score, which is a function indicating a relation between respective estimated results of said first estimation unit and estimated results of said second estimation unit, and age;

an integration unit which outputs an estimated age based on a score obtained by integrating a score of an estimated result of said first estimation unit and a score of an estimated result of said second estimation unit.

2. An age estimation system according to claim 1, wherein said score-generation unit generates the score of the estimated result of said first estimation unit such that said estimated result becomes a fixed value in any one of the plurality of classes.

3. An age estimation system according to claim 1, wherein said score-generation unit generates the score of the estimated result of said first estimation unit such that said estimated result becomes biggest at a median in any one of the plurality of classes, each indicating a predetermined age group, and decreases proportionally to a difference with said median.

4. An age estimation system according to claim 1, wherein said score-generation unit generates the score of the estimated result of said first estimation unit such that said estimated result is of a shape of normal distribution centering on a median in any one of the plurality of classes, each indicating a predetermined age group.

5. An age estimation system according to claim 1, wherein said score-generation unit generates the score of the estimated result of said first estimation unit as distribution of criterion data estimated for any one of the plurality of classes, each indicating a predetermined age group, based on a result which is obtained by performing a reverse lookup of criterion data which said first estimation unit has been used for learning.

6. An age estimation system according to claim 1, wherein said score-generation unit generates the score of the estimated result of said first estimation unit such that said estimated result becomes a fixed value within each of the plurality of classes indicates a predetermined age group based on a probability corresponding to each of the plurality of classes.

7. An age estimation system according to claim 1, wherein said score-generation unit generates for each of the plurality of classes, indicating a predetermined age group, the score of the estimated result of said first estimation unit such that said estimated result becomes biggest at a median in each of the plurality of classes, and decreases proportionally to a difference with said median based on a probability corresponding to each class, and wherein said score-generation unit accumulates the scores to generating a score.

8. An age estimation system according to claim 1, wherein said score-generation unit generates for each of the plurality of classes, indicating a predetermined age group, a score of the estimated result of said first estimation unit such that said estimated result is of a shape of normal distribution centering on a median in the each of the plurality of classes based on a probability corresponding to each of the plurality of classes; and wherein said score-generation unit accumulates the scores to generating a score.

9. An age estimation system according to claim 1, wherein said score-generation unit generates the score of the estimated result of said first estimation unit as distribution of criterion data estimated for each of the plurality of classes, each indicating a predetermined age group, according to a probability corresponding to each of the plurality of classes based on a result which is obtained by performing a reverse lookup of criterion data which said first estimation unit has been used for learning.

10. An age estimation system according to claim 1, wherein said score-generation unit generates the score of the estimated result of said second estimation unit as a fixed value within a predetermined age group which takes an estimated result of said second estimation unit as a median.

11. An age estimation system according to claim 1, wherein said score-generation unit generates the score of the estimated result of said second estimation unit such that said estimated result becomes biggest at a point of an estimated result of said second estimation unit, and decreases proportionally to a difference with said estimated result of said second estimation unit.

12. An age estimation system according to claim 1, wherein said score-generation unit generates the score of the estimated result of said second estimation unit as a form of normal distribution centering on an estimated result of said second estimation unit.

13. An age estimation system according to claim 1, wherein said score-generation unit generates the score of the estimated result of said second estimation unit as distribution of criterion data estimated for a certain age based on a result which is obtained by performing a reverse lookup of criterion data which said second estimation unit has been used for learning.

14. An age estimation system according to claim 1, wherein at least one piece of said input data is image data and an age of a person photographed in said image is estimated.

15. An age estimation system according to claim 1, wherein a plurality of images are included as said input data and an age of a person who has been photographed in common in said plurality of images is estimated.

16. An age estimation system according to claim 1, wherein at least one piece of said input data is voice data.

17. An age estimation system according to claim 1, wherein said integration unit outputs a peak value in an integration result of a score of an estimated result of said first estimation unit and a score of an estimated result of said second estimation unit as an estimated age.

18. An age estimation system according to claim 1, wherein said integration unit outputs a class indicating a predetermined age group to which a peak value in an integration result of a score of an estimated result of said first estimation unit and a score of an estimated result of said second estimation unit belongs as an estimated age.

19. An age estimation system according to claim 1, wherein said integration unit performs integral calculation of an integration result of a score of an estimated result of said first estimation unit and a score of an estimated result of said second estimation unit for each of the plurality of classes, indicating a predetermined age group, and outputs a class in which an value obtained by performing said integral calculation takes a maximum value as an estimated age.

20. An age estimation method for estimating an age based on at least one piece of input data, comprising;
    extracting at least one first feature from said input data;
    estimating said age as a discrete quantity based on the at least one first feature;
    extracting at least one second feature from said input data;
    estimating said age as a continuous quantity based on the at least one second feature
    generating a score which is a function indicates a relation between respective results estimated as the discrete quantity and results estimated as the continuous quantity, and age; and
    outputting an estimated age based on a score obtained by integrating a score of a result estimated as the discrete quantity and a score of a result estimated as the continuous quantity.

* * * * *